United States Patent [19]
Fattore et al.

[11] 3,983,054
[45] Sept. 28, 1976

[54] CATALYTIC COMPOSITION AND ITS APPLICATIONS TO THE PRODUCTION OF UNSATURATED NITRILES AND TO THE OXIDATION OF OLEFINES

[75] Inventors: Vittorio Fattore; Bruno Notari, both of San Donato Milanese, Italy

[73] Assignee: Snam Progetti S.p.A., Milan, Italy

[22] Filed: July 26, 1974

[21] Appl. No.: 492,222

Related U.S. Application Data

[62] Division of Ser. No. 133,886, April 14, 1971, Pat. No. 3,850,975.

[30] Foreign Application Priority Data

Apr. 14, 1970 Italy................................... 23270/70

[52] U.S. Cl............................. 252/439; 260/465.3; 423/508

[51] Int. Cl.$^2$................. B01J 27/02; C07C 120/14; C01B 19/00

[58] Field of Search....................... 252/439; 423/508

[56] References Cited
UNITED STATES PATENTS

| | | | |
|---|---|---|---|
| 3,849,337 | 11/1974 | Manara et al....................... | 252/439 |
| 3,850,975 | 11/1974 | Fattore et al. .................. | 252/439 X |

Primary Examiner—Winston A. Douglas
Assistant Examiner—William G. Wright
Attorney, Agent, or Firm—Ralph M. Watson

[57] ABSTRACT

A catalyst useful in the ammoxidation or oxidation of olefins consisting of a mixture of uranium oxide and tellurium oxide wherein the Te/U atomic ratio is in the range from 2 to 5. Also disclosed is a catalyst as defined above which is supported on a carrier.

5 Claims, 1 Drawing Figure

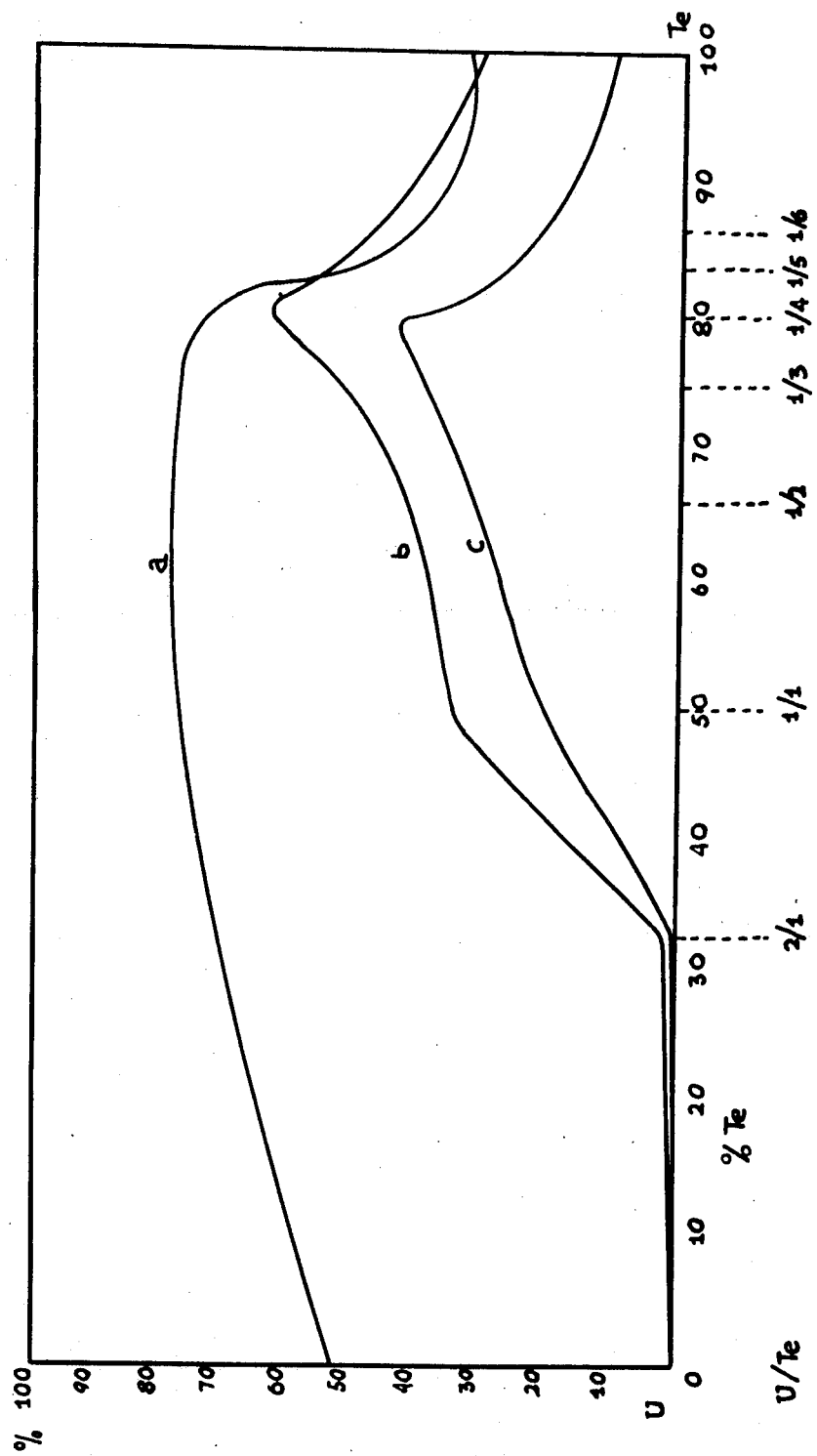

CATALYTIC COMPOSITION AND ITS APPLICATIONS TO THE PRODUCTION OF UNSATURATED NITRILES AND TO THE OXIDATION OF OLEFINES

This is a division, of application Ser. No. 133,886, filed Apr. 14, 1971 U.S. Pat. No. 3,850,975.

The present invention relates to a catalytic composition and to its application in the production of unsaturated nitriles starting from olefins and to the oxidation of olefins. For simplicity, hereinafter we refer to the case wherein the olefin is propylene, the unsaturated nitrile is acrylonitrile and the oxygen compound is acrolein.

It is known that for the industrial production of acrylonitrile starting from propylene, ammonia and air or oxygen the binary catalytic systems Bi-Mo, U-Sb, Sn-Sb and the ternary catalytic systems Te-Ce-Mo, Bi-V-Mo are used, all catalytic systems supported on a silica carrier. Certain interesting results have been obtained by means of catalytic compositions classifiable in the families of molybdenum and antimony catalysts.

In the prior art many examples of catalysts containing uranium are known, which catalysts are useful for the preparation of unsaturated nitriles and in particular acrylonitrile. Among them is: uranium oxide (U.S. Pat. No. 2,481,826); various uranium compounds used as activators of catalysts comprised of "solid phosphoric acids" (British Pat. No. 957,022); uranium, either metallic or in the form of the oxide or of another compound together with one or more oxy compounds of other elements (Italian Pat. No. 483,174); Sb-U catalysts activated by oxygen compounds of metals having an atomic number from 22 to 41, from 44 to 49, 73, from 77 to 83 and 90 (British Pat. No. 1,007,929); U-Sb-Sn catalysts (British Pat. No. 1,026,477); catalysts containing uranium oxide or other heavy metal oxides together with the couple Sb-V (Belgian Pat. 712,931); catalysts comprising $moO_3$-$TeO_2$ and a phosphate of heavy metals (for instance uranium) having the general formula $Mo_{10} Te_{1-10} M_{2-20} P_{2-20} O_{39-120}$ where M can be also uranium and phosphorus is bound to 3 or 4 oxygen atoms (French Pat. No. 1,491,652); catalysts (Italian Pat. No. 682,880) comprised in their active part by at least a heteropolyacid, the element thereof constituting the coordinating radical having acid character, selected from the elements of the rare earths of the lanthanum series, e.g., lanthanum and cerium, and of the actinide series, e.g., thorium, and the coordinating radical being coordinated with tungsten and/or molybdenum salified with at least one element selected from uranium, antimony, bismuth, tin, copper, tellurium. Other catalysts containing uranium are known. For instance in U.S. Pat. No. 3,198,750 and U.S. Pat. No. 3,328,315 the U-Sb couple is mentioned. All these catalysts with the exclusion of those of Italian Pat. No. 682,880 do not have tellurium in their composition while the aforementioned Italian Patent has it in a complicated formulation. A catalyst based on tellurium oxide is also known.

With respect to conversion, selectivity and acrylonitrile yield in ammoxidation of propylene according to the reaction:

$$C_3H_6 + NH_3 + 1.5 O_2 \rightarrow C_3H_3N + 3 H_2O$$

using uranium oxide or tellurium oxide as catalyst, the following formulae will be used Conversion % $C_3H_6$ = $\dfrac{\text{moles } C_3H_6 \text{ in - moles } C_3H_6 \text{ out}}{\text{moles } C_3H_6 \text{ in}} \cdot 100$ Selectivity % ACN = $\dfrac{\text{moles acrylonitrile produced}}{\text{moles } C_3H_6 \text{ in - moles } C_3H_6 \text{ out}} \cdot 100$ Yield % ACN = $\dfrac{\text{moles acrylonitrile produced}}{\text{moles } C_3H_6 \text{ in}} \cdot 100$ moles $C_3H_6$ in - moles $C_3H_6$ entering the reactor; moles $C_3H_6$ out - moles $C_3H_6$ leaving the reactor. (ACN - acrylonitrile).

Uranium oxide is very active; it converts the oxygen fed into the reactor to $CO_2$, CO and $H_2O$. It does not present any selectivity for intermediate oxidation products and has the tendency to be reduced by ammonia and propylene in the reaction conditions. Tellurium oxide is mush less active (maximumpropylene conversion 33%) but presents a fairly good selectivity towards acrylonitrile, about 45%, which value is cited in the literature for metal oxides. So, said catalysts do not appear to be particularly suitable for the production of acrylonitrile starting from propylene.

The subject of the present invention is a catalyst comprising a mixture of U and Te as oxides or oxygenated compounds suitable for the preparation of unsaturated nitriles starting from olefins, ammonia and oxygen or air. We have in fact surprisingly found that mixtures of oxides or oxygenated compounds of uranium and tellurium furnish catalysts having a high selectivity towards acrylonitrile and very good yield. These oxides or oxygenated compounds may be supported on catalyst carrier such as silica or other such conventional material. It is to be noted that this is surprising because not all the mixtures of the two said oxides are utilizable according to the invention.

In a preferred embodiment of the invention the catalytic mixtures have atomic ratios Te/U ranging from 3 to 4.5. It is possible for the ratio to range from 2 to 5. By examining the behavior of U-Te mixtures, we noted that over the ratio U/Te = 2 we obtained as in the case of uranium oxide, almost exclusively a propylene combustion. When U/Te ratio is 1 we obtained a selectivity toward acrylonitrile of 40%. By increasing the tellurium amount in comparison with uranium amount selecting Suitable working conditions the highest selectivity was reached for U/Te ratio = ¼. By adding more tellurium the obtained results indicated a sharp decrease to values of the same magnitude order of the ones of telluium oxide. In the Figure conversion, (curve a), selectivity (curve b) and yields (curve c) are plotted as a function of different tellurium percentages in U/Te catalysts. As to silica percentages in the catalytic mixture they may reach 80%.

A further object of the present invention is a process for the production of an unsaturated nitrile starting from an olefin, ammonia and air or oxygen use being made of the invention catalyst. In particular we refer to the case wherein, the olefin is propylene and the nitrile is acrylonitrile, although the process is useful to the production of other unsaturated nitriles. The mixture in vapor phase of propylene, ammonia and oxygen or air having the ammonia/propylene molar ratio of from 0.05/1 to 5/1 and preferably of from 0.7/1 to 1.5/1 and an oxygen/propylene ratio ranging from 0.5/1 to 3/1, preferably from 1/1 to 2/1, is fed, preferably in presence of steam, to a reactor with a fixed or fluid catalyst bed, the temperature being in the range of from 300°C to 500°C, preferably of from 350°C to 490°C and the pressure being atmospheric or slightly higher than atmospheric.

The contact time ranges from 0.1 to 50 sec, preferably from 1 to 15 sec; for contact time we mean the ratio between the catalyst volume and the volumetric rate of the reaction gases fed to the reactor, volumes being expressed in cc., time in seconds and the gases being in standard conditions of temperatures and pressure. The unreacted feed may be recovered from the reaction products by any of the known means, as for instance by treatment with cold water or a suitable solvent. Conversions and selectivities in the described process by means of the aforesaid catalyst are industrially interesting.

Another object of the present invention is a process for the production of oxygenated compounds starting from olefins and oxygen. In particular we refer to the case wherein the olefin is propylene and the oxygenated compound is acrolein. The mixture in vapor state of propylene, air and oxygen is fed, in presence of steam, to a fluid or fixed catalyst bed reactor wherein the temperature is in the range of from 350°C to 500°C, preferably of from 390°C to 480°C and the pressure is the atmospheric one or slightly higher than the atmospheric one. The contact time ranges from 0.1 to 50 sec, and preferably from 1 to 15 sec, conversion and selectivities being industrially interesting. For illustrative but not limitative purposes we are now reporting the results obtained in some tests carried out with the catalytic mixture object of the present invention.

Example 1 a. Preparation of the U-Te catalyst object of the present invention. 50 g. of $UO_2(NO_3)_2.6 H_2O$ are weighed and transferred in a glass. 50 g. of distilled water are added. The solution is stirred by means of a magnetic stirrer up to a complete dissolution of the salt. 92 g. of telluric acid $H_2TeO_4. 2 H_2O$ are separately dissolved in 100 cc of distilled water following the same procedure. The two solutions are mixed by pouring the first one into the second one and then are heated by an electric plate under continuous stirring up to dryness. The capsule containing the dry substances was put into a muffle where the catalyst calcination and activation was carried out at 530°C for 4 hours in an air stream.

The solid was let cool and then was ground in a mortar and the fraction having a granulometry in the range of from 45 to 100 ASTM recovered.

b. In the following table data are reported obtained by means of a catalyst prepared as described in a) in the propylene ammoxidation. We used 6 cc of catalyst activated at the defined temperature having a size of 45–100 mesh. Under the catalyst we put about 1 cc of quartz having a granulometry of 80–150 mesh and on the catalyst 7-8 cc of quartz having a granulometry of 10-20 mesh. The reactants were fed in the molar ratio air/ammonia/propylene of 12/1.1/1. In the following table we report the experimental results of the test.

| Catalyst: Atomic Ratio U/Te | | ¼ | |
|---|---|---|---|
| Temperature (°C) | 460 | 460 | 460 |
| Propylene Space Velocity (cc/cch) | 50 | 25 | 12.5 |
| Conversion $C_3H_4$ (% by moles) | 36 | 50.2 | 72.4 |
| Acrylonitrile Yield (% by moles) | 20.5 | 31 | 45 |
| Acrylonitrile Selectivity (% by moles) | 56.6 | 61.7 | 62.2 |
| Acetonitrile Selectivity (% by moles) | 3.9 | 1 | 0.9 |
| Acrolein Selectivity (% by moles) | 1.8 | 1.5 | 0.4 |

Example 2 a. Method for the preparation of the supported catalyst object of the present invention. 100 g. of $UO_2(NO_3)_2.6 H_2O$ were dissolved in 200 cc of distilled water. Separately 160 g. of telluric acid ($H_2TeO_4$) were dissolved in 200 cc of distilled water and then added to the first solution. 184 g. of a solution with 30% silica (Ludox A. S.) were weighed; to said solution the solution containing the uranium and tellurium compounds was added always under continuous stirring. The obtained solution was then fed to a mini-spray-dryer where it was instantaneously dried. The obtained dust was recovered and tabletted. The tablets were calcinated at 530°C in a muffle for 4 hours in an air stream. The catalyst was let cool and then ground in a mortar; the fraction having a granulometry in the range of from 35 to 120 mesh ASTM was recovered for subjecting the same to the ammoxidation reaction. Said catalyst was constituted by 75% of active part wherein uranium and tellurium were in the atomic ratio of 1/4 and by 25% of silica ($SiO_2$).

b. In the following table data are reported obtained in the olefins ammoxidation with a catalyst having different silica percentages, a method of preparation thereof being given at point a). The catalyst conditions in the reactor are the same as Example 1.

| Ammoxidation of Propylene | | | | | | | |
|---|---|---|---|---|---|---|---|
| Catalyst: Atomic Ratio U/Te | | ¼ | | | ¼ | | |
| % Silica Carrier in the Catalyst | | 25% | | | 50% | | |
| Temperature (°C) | 430 | 450 | 450 | 450 | 445 | 430 | 440 |
| Propylene Space Velocity (cc/cch) | 50 | 50 | 25 | 40 | 25 | 12.5 | 12.5 |
| Feed: Ratio $C_3H_6$/Air/$NH_3$ | 1/12/1.1 | 1/12/1.1 | 1/12/1.1 | 1/12/1.1 | 1/12/1.1 | 1/12/1.1 | 1/12/1.1 |
| Conversion $C_3H_6$ (% by moles) | 51.1 | 67.7 | 84.3 | 47.6 | 67 | 76.8 | 81 |
| Acrylonitrile Yield (% by moles) | 35.4 | 44 | 53.5 | 25.4 | 37.5 | 43 | 47.4 |
| Acrylonitrile Selectivity (% by moles) | 69.4 | 65.2 | 63.4 | 53.4 | 56 | 56 | 58.4 |
| Acrylonitrile Selectivity (% by moles) | 0.4 | 0.4 | 0.8 | 1.6 | 0.8 | 2.1 | 1.3 |
| Acrolein Selectivity (% by moles) | 3.6 | 5.2 | 1 | 3.5 | 1.7 | 0.5 | 0.8 |

Example 3

A catalyst prepared according to the procedure described in part a) of Example 2 was used for oxidizing propylene. Said catalyst had 25% silica and presented an atomic ratio uranium/tellurium of 1/4. In a microreactor 6 cc of said catalyst were fed. Temperature in microreactor was raised up to 430°C by means of a small electrical furnace; a mixture of air, steam and propylene was fed, in a ratio of 12/5/1 with a propylene space velocity of 25 cc/cch calculated at atmospheric pressure and room temperature. The catalyst was stabilized in reaction for 10 hours. The chromatography analysis carried out on the gases produced during the reaction gave the following results:

Propylene conversion: 78.5% by moles
Acrolene selectivity: 57.5% by moles

What we claim is

1. A catalyst composition consisting of a mixture of uranium oxide and tellurium oxide wherein the Te/U atomic ratio is in the range from 2 to 5.
2. A catalyst composition as defined in claim 1 wherein said Te/U atomic ratio is in the range from 3 to 4.5.
3. A catalyst composition as defined in claim 1 wherein the catalyst is supported on a carrier.
4. A catalyst as defined in claim 3 wherein said carrier is silica which constitutes up to 80% of the catalyst composition.
5. A catalyst as defined in claim 4 wherein silica comprises 25% of the catalyst composition.

* * * * *